(12) United States Patent
Fujii et al.

(10) Patent No.: US 9,499,696 B2
(45) Date of Patent: Nov. 22, 2016

(54) COLORED METALLIC PIGMENT AND METHOD FOR PRODUCING THE SAME

(75) Inventors: Miki Fujii, Osaka (JP); Shunichi Setoguchi, Osaka (JP); Yoshiki Hashizume, Osaka (JP)

(73) Assignee: TOYO ALUMINUM KABUSHIKI KAISHA, Osaka-shi (JP)

( * ) Notice: Subject to any disclaimer, the term of this patent is extended or adjusted under 35 U.S.C. 154(b) by 0 days.

(21) Appl. No.: 14/374,615

(22) PCT Filed: Sep. 14, 2012

(86) PCT No.: PCT/JP2012/073694
§ 371 (c)(1),
(2), (4) Date: Jul. 25, 2014

(87) PCT Pub. No.: WO2014/041692
PCT Pub. Date: Mar. 20, 2014

(65) Prior Publication Data
US 2015/0071973 A1    Mar. 12, 2015

(51) Int. Cl.
| | |
|---|---|
| *C09C 1/62* | (2006.01) |
| *C09C 1/64* | (2006.01) |
| *C09C 3/00* | (2006.01) |
| *A61K 8/02* | (2006.01) |
| *B05D 5/06* | (2006.01) |
| *C09C 3/08* | (2006.01) |
| *C09C 3/10* | (2006.01) |
| *C09D 7/12* | (2006.01) |

(52) U.S. Cl.
CPC .............. *C09C 3/006* (2013.01); *A61K 8/0241* (2013.01); *B05D 5/068* (2013.01); *C09C 1/62* (2013.01); *C09C 1/644* (2013.01); *C09C 3/08* (2013.01); *C09C 3/10* (2013.01); *C09D 7/125* (2013.01); *A61K 2800/43* (2013.01); *A61K 2800/63* (2013.01); *A61K 2800/651* (2013.01); *C01P 2006/65* (2013.01)

(58) Field of Classification Search
CPC ............ C09C 1/62; C09C 3/06; C09C 3/006; C09C 1/64; C09C 1/644; C09D 7/125; A61K 8/0241
See application file for complete search history.

(56) References Cited

U.S. PATENT DOCUMENTS

| | | |
|---|---|---|
| 5,037,475 A | 8/1991 | Chida et al. |
| 5,931,996 A | 8/1999 | Reisser et al. |
| 2002/0160194 A1* | 10/2002 | Phillips ............... B41M 3/14 428/403 |
| 2005/0147821 A1 | 7/2005 | Hashizume et al. |
| 2007/0104663 A1 | 5/2007 | Henglein et al. |
| 2008/0081864 A1 | 4/2008 | Takano |
| 2008/0115693 A1 | 5/2008 | Hashizume |
| 2008/0118448 A1 | 5/2008 | Kruger |
| 2009/0131584 A1 | 5/2009 | Terao et al. |
| 2011/0195244 A1 | 8/2011 | Setoguchi et al. |
| 2012/0065298 A1 | 3/2012 | Setoguchi |
| 2012/0129998 A1 | 5/2012 | Nakao et al. |
| 2013/0131187 A1 | 5/2013 | Hashizume et al. |

FOREIGN PATENT DOCUMENTS

| | | | |
|---|---|---|---|
| CN | 1185798 A | 6/1998 | |
| CN | 101133128 A | 2/2008 | |
| CN | 102159652 A | 8/2011 | |
| JP | 53-77225 | 7/1978 | |
| JP | 58-141248 A | 8/1983 | |
| JP | 1-153761 A | 6/1989 | |
| JP | 5-508424 A | 11/1993 | |
| JP | 9-40885 A | 2/1997 | |
| JP | 9-59532 A | 3/1997 | |
| JP | 9-124973 A | 5/1997 | |
| JP | 1-315470 A | 12/1998 | |
| JP | 10-513206 A | 12/1998 | |
| JP | 2000-005695 A | 1/2000 | |
| JP | 2003-292825 A | 10/2003 | |
| JP | 2005-255984 | * 9/2005 | ............... C09C 1/00 |
| JP | 2005-255984 A | 9/2005 | |
| JP | 2005-264144 A | 9/2005 | |
| JP | 2006-199920 A | 8/2006 | |
| JP | 2007-119671 A | 5/2007 | |
| JP | 2007-511655 A | 5/2007 | |
| JP | 2007-515526 A | 6/2007 | |
| JP | 2008-201821 A | 9/2008 | |
| JP | 2010-70617 A | 4/2010 | |
| JP | 2010-270281 A | 12/2010 | |
| JP | 2011-12223 A | 1/2011 | |
| JP | 2011-157516 A1 | 8/2011 | |
| JP | 2012-31232 A | 2/2012 | |
| WO | WO 91/04293 A1 | 4/1991 | |
| WO | WO 96/38506 A1 | 12/1996 | |
| WO | WO 2006/090431 A1 | 8/2006 | |
| WO | WO 2012/014573 A1 | 2/2012 | |

OTHER PUBLICATIONS

Chinese Office Action issued in the counterpart Chinese Patent Application No. 2012800711229, mailed on Dec. 21, 2015, along with English translations.

* cited by examiner

*Primary Examiner* — Pegah Parvini
(74) *Attorney, Agent, or Firm* — Birch, Stewart, Kolasch & Birch, LLP

(57) ABSTRACT

A colored metallic pigment of the present invention includes a metallic pigment, a first coating layer formed on the surface of the metallic pigment, and a coloring pigment adhered to the surface of the first coating layer. The first coating layer is formed from radical-polymerizable resin or a first compound, and the first compound is an oxide or a hydroxide of at least one element selected from the group consisting of Al, Si, Ti, Cr, Zr, Mo and Ce.

12 Claims, No Drawings

COLORED METALLIC PIGMENT AND METHOD FOR PRODUCING THE SAME

TECHNICAL FIELD

The present invention relates to a colored metallic pigment used in metallic coating finish of an automobile or the like, decorative finish of a plastic material, print ink and a cosmetic preparation, particularly relates to a colored metallic pigment superior in water resistance so as to be used in a water-based paint or water-based ink, and further relates to a paint composition, a plastic material and a cosmetic preparation each formulated with the colored metallic pigment.

BACKGROUND ART

A colored metallic pigment having a coloring pigment adhered to a metallic pigment such as aluminum pigment, due to its performance superior in offering a vivid color tone and the hiding power of hiding underlying color, is being applied to such as a paint for an automobile, a plastic decoration, print ink and a cosmetic preparation.

For example, Japanese Patent Laying-Open No. 58-141248 (PTD 1) proposes a colored metallic pigment prepared by homogeneously adhering a coloring pigment to the surface of a metallic pigment with a polymer composed of a monomer having polymerizable double bonds, Japanese National Patent Publication No. 05-508424 (PTD 2) proposes a coloring pigment composed of a combination of fragments of metal in particular and a polymer matrix held thereon for pocketing a solid colored metallic pigment, Japanese Patent Laying-Open No. 01-315470 (PTD 3) proposes a colored metallic pigment prepared by chemisorbing a coloring pigment onto the surface of a metallic pigment through a carboxylic acid which has at least one double bond and at least two carboxyl groups and is prepared by thermally polymerizing at least one carboxylic acid having double bonds, Japanese Patent Laying-Open No. 09-040885 (PTD 4) proposes a surface-treated coloring pigment prepared by coating the surface of a coloring pigment with 0.2 to 100 parts by weight of monobasic aromatic carboxylic acid with respect to 100 parts by weight of the coloring pigment, Japanese Patent Laying-Open No. 09-059532 (PTD 5) proposes a colored metallic flake pigment having a vapor-deposited layer of an organic coloring pigment on the surface thereof, and Japanese Patent Laying-Open No. 09-124973 (PTD 6) proposes a surface-treated coloring pigment prepared by coating the surface of a coloring pigment with 0.2 to 100 parts by weight of an amino compound having two amino groups but no carboxyl group in each molecule with respect to 100 parts by weight of the coloring pigment.

Japanese Patent Laying-Open No. 2006-199920 (PTD 7) and Japanese Patent Laying-Open No. 2005-264144 (PTD 8) disclose a highly corrosion-resistant metallic luster coloring pigment which forms color according to optical interference and is prepared by forming on the surface thereof a hydrated metal oxide layer and thereafter disposing a second hydrated metal oxide layer formed from iron oxide or the like on the hydrated metal oxide layer.

WO 2006/090431 pamphlet (PTD 9) discloses a colored metallic pigment having a coloring pigment adhered onto a metallic pigment adhered with a metal oxide for the purpose of reducing light reflectance in a wavelength range of 300 to 600 nm.

Japanese National Patent Publication No. 10-513206 (PTD 10) discloses a colored aluminum pigment coated with a metal oxide layer characterized in that the metal oxide layer contains an organic pigment.

CITATION LIST

Patent Document

PTD 1: Japanese Patent Laying-Open No. 58-141248
PTD 2: Japanese National Patent Publication No. 05-508424
PTD 3: Japanese Patent Laying-Open No. 01-315470
PTD 4: Japanese Patent Laying-Open No. 09-040885
PTD 5: Japanese Patent Laying-Open No. 09-059532
PTD 6: Japanese Patent Laying-Open No. 09-124973
PTD 7: Japanese Patent Laying-Open No. 2006-199920
PTD 8: Japanese Patent Laying-Open No. 2005-264144
PTD 9: WO 2006/090431 pamphlet
PTD 10: Japanese National Patent Publication No. 10-513206

SUMMARY OF INVENTION

Technical Problem

The colored metallic pigment proposed in each of PTDs 1 to 6 is prepared by having a coloring pigment adhered directly or through a specific compound to the surface of a metallic pigment and coating the coloring pigment with resin to fix the coloring pigment, and thereby, it is easy that defects may occur in the resin which functions as a water-resistant protection film, making the water resistance insufficient. Particularly in PTD 3, the colored metallic pigment is chemisorbed after polymer resin is formed through thermal polymerization on the surface of the metallic pigment (metal pigment), the colored metallic pigment has such structure that the metallic pigment is coated only by resin containing no coloring pigment, and thereby, it is expected that the water resistance can be improved to some extent in comparison to those proposed by the other patent documents. However, it is difficult to form the thermally polymerized polymer resin into a dense coating film. Thus, even though the colored metallic pigment proposed by PTD 3 is used, in the case where it is used in a water-based paint or water-based ink, the application of which is increasing in recent years as a countermeasure to environmental issues, there is such a problem that the metallic pigment, namely the base material of the colored metallic pigment reacts with water, releasing hydrogen gas.

On the other hand, although the colored metallic pigment proposed in PTDs 7 and 8 is stable in a water-based paint or water-based ink, since the development of color is based on interference action of light rays in each layer, there is such a problem that it is impossible for it to provide a color tone as vivid as that provided by the colored metallic pigment proposed in each of PTDs 1 to 6 and the color phase thereof is also limited.

Further, the colored metallic pigment proposed in PTD 9 is aimed to prevent the coloring pigment from being optically deteriorated by lights reflected from the surface of the metallic pigment, without being designed to improve the water resistance of the colored metallic pigment.

Furthermore, the colored metallic pigment proposed in PTD 10 has the coloring pigment dispersed in the metal oxide layer coating the metallic pigment, the color saturation is therefore weak compared with the original color of the coloring pigment itself, and moreover, since the metallic pigment serving as the base material is covered by the metal oxide layer, the colored metallic pigment is stable even in a water-based paint or in water-based ink; however, in the case where the pigment is present on the outmost surface, it is detached easily when being dispersed to a paint or a solvent, which may affect the color tone or the performance of the composition.

The present invention has been accomplished in view of the aforementioned problems, and it is therefore an object of the present invention to provide a colored metallic pigment superior in water resistance and stable color development, and a method for producing the same.

Solution to Problem

After various researches on the above problems, the inventors of the present invention found that it is possible to obtain a colored metallic pigment superior in water resistance and stable color development by preliminarily forming a dense coating film superior in water resistance on the surface of a metallic pigment and thereafter adhering a coloring pigment thereon, and thereby accomplished the present invention.

Specifically, the colored metallic pigment according to the present invention contains a metallic pigment, a first coating layer formed on the surface of the metallic pigment, and a coloring pigment adhered to the surface of the first coating layer. The first coating layer is formed from radical-polymerizable resin or a first compound, and the first compound is an oxide or a hydroxide of at least one element selected from the group consisting of Al, Si, Ti, Cr, Zr, Mo and Ce.

It is preferable that the coloring pigment is adhered to the surface of a layer of an organic compound having a phosphate group or a carboxyl group, the layer of the organic compound being formed on the first coating layer, and it is preferable that the organic compound having a carboxyl group is a carboxylic acid having at least one double bond and two or more carboxyl groups, or a polymer of the carboxylic acid, and it is preferable that the organic compound having a phosphate group is an organic phosphate compound having at least one polymerizable double bond.

It is preferable that the colored metallic pigment according to the present invention further has a second coating layer formed on the coloring pigment, and it is preferable that the metallic pigment is aluminum pigment.

It is preferable that the radical-polymerizable resin is prepared by subjecting a monomer and/or an oligomer having at least one polymerizable double bond to radical polymerization, and it is preferable that the first compound is silicon oxide and/or polysiloxane condensate. Further, it is preferable that the second coating layer is formed from the radical-polymerizable resin or the first compound.

The present invention also relates to a method for producing a colored metallic pigment. The method includes a first step of preparing a coated metallic pigment having a first coating layer formed on the surface of a metallic pigment, and a second step of adhering a coloring pigment to the surface of the first coating layer of the coated metallic pigment. The first coating layer is formed from radical-polymerizable resin or a first compound, and the first compound is an oxide or a hydroxide of at least one element selected from the group consisting of Al, Si, Ti, Cr, Zr, Mo and Ce.

It is acceptable that the method for producing the colored metallic pigment includes an additional step of forming, on the surface of the first coating layer of the coated metallic pigment, a layer of an organic compound having a phosphate group or a carboxyl group after the first step and the coloring pigment, in the second step, is adhered to the organic compound layer formed in the additional step.

The present invention also relates to a paint composition, a plastic material and a cosmetic preparation, each of which is formulated with the colored metallic pigment mentioned above.

Advantageous Effects of Invention

Since the colored metallic pigment according to the present invention has the abovementioned configurations, it is superior in water resistance and thereby sufficiently stable in a water-based paint or water-based ink without releasing hydrogen gas, and it is possible to obtain stable color development and a design of high color saturation.

DESCRIPTION OF EMBODIMENTS

Hereinafter, the present invention will be described in more detail with reference to the embodiments.

<Colored Metallic Pigment>

The colored metallic pigment of the present invention is basically constituted by a metallic pigment, a first coating layer formed on the surface of the metallic pigment, and a coloring pigment adhered to the surface of the first coating layer. Each constituent element will be described below in more detail.

<Metallic Pigment>

The metallic pigment constituting the colored metallic pigment of the present invention may be any conventionally known metallic pigment as long as it produces metallic feeling, and thereby it is not particularly limited. As examples of the metallic pigment, for example, a metallic pigment formed from metal such as aluminum, zinc, copper, iron, bronze, nickel, titanium or stainless steel, and a metallic pigment formed from an alloy containing those metals may be given.

Among these metallic pigments, aluminum pigment composed of aluminum, high in light reflectance, excellent in metallic luster, low-priced and easy to handle due to its small specific gravity, is particularly preferable. It should be noted that the metallic pigments also include particles which are prepared by forming a metal film through plating or the like on the surface of inorganic compound particles (such as glass, mica or ceramic particles like alumina or titania) so as to produce metallic feeling.

Hereinafter, the description will be carried out on aluminum pigment particularly preferable as the metallic pigment. The aluminum pigment used in the present invention may be formed from aluminum only or from an aluminum-based alloy, and the purity of aluminum is not particularly limited.

Although the shape of the aluminum pigment used in the present invention may have various shapes such as granular, plate-like, aggregated and flaky (scaly) shapes, in order to provide superior metallic feeling and excellent brightness to the coating film, the flaky shape is preferred.

The average particle size of the aluminum pigment used in the present invention, although not particularly limited, is preferably 1 µm or more, and particularly more preferably 5 µm or more. Further, the average particle size is preferably 100 µm or less, and particularly more preferably 50 µm or less.

In the case where the average particle size is 1 µm or more, it is easy to handle in production and it is difficult for the aluminum pigment to agglomerate; and in the case where the average particle size is 100 µm or less, when being used as a paint, it is possible to prevent the film surface from getting rough so as to achieve a preferable design.

Further, the average thickness of the aluminum pigment used in the present invention, although not particularly limited, is preferably 0.02 µm or more, and particularly more preferably 0.1 µm or more. Further, the average thickness of the aluminum pigment is preferably 5 µm or less, and particularly more preferably 2 µm or less. If the average thickness is 0.02 µm or more, it is advantageous in terms of the easy handling in production, and if the average thickness is 5 µm or less, it is advantageous in terms of good outer appearance of a coating composition such as a coating film.

The average particle size of the aluminum pigment used in the present invention is obtained by calculating the volume average from the particle size distribution measured by a publicly known particle size distribution measuring method such as laser diffraction. The average thickness is calculated from the hiding power and the density of the aluminum pigment.

It is acceptable that a grinding aid is adhered to the surface of the aluminum pigment used in the present invention. As the grinding aid, any conventionally known grinding aid may be used without particular limitation.

The method of obtaining the aluminum pigment used in the present invention is not particularly limited, for example, it may be produced by pulverizing or grinding a raw material, namely aluminum powder by using a grinding aid such as aliphatic acid in a ball mill or an attritor mill in the presence of a pulverizing medium, or may be produced by crushing an aluminum vapor-deposited foil which is obtained by vapor-depositing aluminum on a film. As the pulverizing medium, any mineral oil of a high flashing point such as mineral spirit or solvent naphtha may be used.

The above description applies to any metallic pigment other than the aluminum pigment as well.

<First Coating Layer>

The first coating layer of the present invention is formed on the surface of the above metallic pigment, and functions to provide water resistance by densely covering the metallic pigment. The first coating layer is formed from radical-polymerizable resin or a first compound. In the present invention, water resistance refers to such a property that prevents gas from being generated in the case where the colored metallic pigment formulated in a water-based paint or water-based ink contacts water components.

It should be noted that although it is preferable that the first coating layer covers the entire surface of the metallic pigment, even in the case where a part of the surface of the metallic pigment is not covered by the first coating layer due to production conditions or the like, it is not deviated from the scope of the present invention as long as the effects of the present invention can be exhibited.

<Radical-Polymerizable Resin>

Since the radical-polymerizable resin can form an extremely dense coating film in comparison to the thermopolymerized resin in PTD 3 described above, it is possible to improve water resistance dramatically.

In the present specification, the radical-polymerizable resin refers to a high-molecule resin-like compound obtained by subjecting a monomer and/or an oligomer having at least one polymerizable double bond to radical polymerization. Thus, since the radical-polymerizable resin is obtained by subjecting a monomer and/or an oligomer having at least one polymerizable double bond to radical polymerization, by conducting the radical polymerization on the metallic pigment or in the vicinity thereof, it is possible to form the first coating layer on the surface of the metallic pigment from the radical-polymerizable resin. Owing to the stable and dense coating layer formed on the surface of the metallic pigment from the radical-polymerizable resin, the water resistance of the finally obtained colored metallic pigment is improved dramatically.

In the case of forming the first coating layer from the radical-polymerizable resin, the amount of the radical-polymerizable resin is preferably 0.5 to 100 parts by mass, and more preferably 5 to 30 parts by mass with respect to 100 parts by mass of the metallic pigment. The amount of the radical-polymerizable resin may be determined appropriately in consideration of the desired thickness of the first coating layer, the specific surface area of the metallic pigment, the density of the coating radical-polymerizable resin and the like.

Although the thickness of the first coating layer formed from the radical-polymerizable resin is not particularly limited, it is preferably 5 nm or more to 200 nm or less, which is advantageous in terms of the water resistance (which will be insufficient if the thickness is less than 5 nm) of the colored metallic pigment and the outer appearance (which will be deteriorated if the thickness is greater than 200 nm) of the coating composition such as the coating film. As a measuring method, the thickness may be measured through observing sections of the colored metallic pigment by using a scanning electron microscope or the like.

As a specific method of coating the metallic pigment with the radical-polymerizable resin, such method is preferable that a monomer and/or an oligomer, and a polymerization initiator such as benzoyl peroxide, isobutyl peroxide or azobis isobutyronitrile are added to a dispersion prepared by dispersing the metallic pigment in a hydrocarbon-based or alcohol-based solvent (preferably in a hydrocarbon-based solvent), and the mixture is heated under stirring to make the monomer and/or the oligomer undergo the radical polymerization, precipitating the radical-polymerizable resin on the surface of the metallic pigment.

In this case, it is preferable that the added amount of the polymerization initiator is 1 part or more by mass to 30 parts or less by mass with respect to 100 parts by mass of the monomer and/or the oligomer. The polymerization reaction is preferably conducted under oxygen-free atmosphere, for example in an inert gas such as nitrogen or argon. The reaction temperature is preferably in the range of 50 to 150° C., and more preferably in the range of 70 to 100° C. The reaction time is preferably 30 minutes or more to 30 hours or less.

As examples of the monomer and/or the oligomer mentioned above, the followings may be given but it is not limited thereto: acrylic acid, methacrylic acid, methyl methacrylate, butyl acrylate, 2-ethylhexyl acrylate, lauryl acrylate, stearyl acrylate, cyclohexyl acrylate, 2-hydroxyethyl acrylate, 2-hydroxybutyl acrylate, 2-methoxyethyl acrylate, 2-diethylaminoethyl acrylate, butyl methacrylate, octyl methacrylate, 1,4-butanediol diacrylate, 1,6-hexanediol diacrylate, 1,9-nonanediol diacrylate, neopentylglycol diacrylate, tripropyleneglycol diacrylate, tetraethyleneglycol diacrylate, trimethylolpropane triacrylate, tetramethylolmethane tetraacrylate, pentaerythritol triacrylate, trisacryloxyethyl phosphate, ditrimethylolpropane tetraacrylate, styrene, α-methylstyrene, vinyltoluene, divinylbenzene, acrylonitrile, methacrylonitrile, vinyl acetate, vinyl propionate, maleic acid, crotonic acid, itaconic acid, polybutadiene, linseed oil, soybean oil, epoxidized soybean oil, epoxidized polybutadiene, cyclohexenevinyl monoxide, divinylbenzene monoxide, mono(2-acryloyloxyethyl) acid phosphate, mono(2-methacryloyloxyethyl) acid phosphate, 2-acryloyloxyethyl acid phosphate, 2-methacryloyloxyethyl acid phosphate, (2-hydroxyethyl) methacrylate acid phosphate, 2-methacryloyloxyethyl acid phosphate, 2-acryloyloxyethyl acid phosphate, diphenyl-2-methacryloyloxyethyl acid phosphate, diphenyl-2-acryloyloxyethyl acid phosphate, dibutyl-2-methacryloyloxyethyl acid phosphate, dibutyl-2-acryloyloxyethyl acid phosphate, dioctyl-2-methacryloyloxyethyl acid phosphate, dioctyl-2-acryloyloxyethyl acid phosphate, 2-methacryloyloxy propyl acid phosphate, bis(2-chloroethyl) vinyl phosphonate, di-2-methacryloyloxyethyl acid phosphate, tri-2-methacryloyloxyethyl acid phosphate, di-2-acryloyloxyethyl acid phosphate, tri-2-acryloyloxyethyl acid phosphate, diallyl dibutyl phosphono succinate, acrylic modified polyester (polymerization degree of about 2 to 20), acrylic modified polyether (polymerization degree of about 2 to 20), acrylic modified urethane (polymerization degree of about 2 to 20), acrylic modified epoxy(polymerization degree of about 2 to 20), acrylic modified spirane (polymerization degree of about 2 to 20), and the like.

Among those, in the case where a monomer and/or an oligomer having two or more polymerizable double bonds is used as the monomer and/or the oligomer, the first coating layer is formed from radical-polymerizable resin cross-linked in three dimensions, which is advantageous in terms of further improving the water resistance.

The identification that whether or not the first coating layer is formed from the radical-polymerizable resin in the colored metallic pigment can be determined according to the remaining group analysis on the polymerization initiator by mass spectrometry, NMR or the like, and more simply according to the molecular weight, the molecular weight distribution, the glass-transition temperature, the solubility to organic solvent and the like.

<First Compound>

The first compound forming the first coating layer is an oxide or a hydroxide of at least one element selected from the group consisting of Al, Si, Ti, Cr, Zr, Mo and Ce. The use of the first compound allows a dense coating film, which is stable against water, to be formed on the surface of the metallic pigment, dramatically improving the water resistance of the colored metallic pigment obtained finally. It should be noted that the first compound is preferably colorless for the purpose of not interfering with the color development of the coloring pigment to be adhered later.

As specific examples of the first compound, silicon oxide, polysiloxane condensate, aluminum oxide, titanium oxide, aluminum hydroxide, molybdenum oxide, chromium oxide, zirconium oxide, zirconium hydroxide, cerium oxide and cerium hydroxide, for example, may be given. Among these, silicon oxide and/or polysiloxane condensate (i.e., silicon oxide alone, polysiloxane condensate alone, and a mixture of both) is preferable in terms of transparency, safety and production cost.

The first compound mentioned above may be used to form the first coating layer in only one compound or a mixture of two or more compounds. It should be noted that silicon oxide and polysiloxane condensate are both oxides of Si, and polysiloxane condensate is a compound obtained through condensation of organic silicon compounds by siloxane bond.

The amount of the first compound is preferably 0.5 parts or more by mass to 100 parts or less by mass, and more preferably 5 parts or more by mass to 30 parts or less by mass with respect to 100 parts by mass of the metallic pigment. The amount of the first compound may be determined appropriately in consideration of the thickness of the first coating layer, the specific surface area of the metallic pigment, the density of the first compound to be coated and the like. Although the thickness of the first coating layer formed from the first compound is not particularly limited, it is preferably 5 nm or more to 200 nm or less, which is advantageous in terms of the water resistance (which will be insufficient if the thickness is less than 5 nm) of the colored metallic pigment and the outer appearance (which will be deteriorated if the thickness is greater than 200 nm) of the coating composition such as the coating film. The thickness may be determined according to a measuring method through observing sections of the colored metallic pigment by using a scanning electron microscope or the like.

The method of coating the metallic pigment with the first compound is not particularly limited, and such method can be given as an example in which a precursor of the first compound, such as salt or alkoxide of any of Al, Si, Ti, Cr, Zr, Mo and Ce is added to a dispersion prepared by dispersing the metallic pigment in water and/or a hydrophilic solvent, and thereafter a neutralizing agent for neutralizing the precursor or a hydrolysis catalyst for hydrolyzing the precursor is added so as to precipitate the first compound on the surface of the metallic pigment.

As examples of the hydrophilic solvent mentioned above, the followings may be given: methyl alcohol, ethyl alcohol, isopropyl alcohol, n-propyl alcohol, t-butyl alcohol, n-butyl alcohol, isobutyl alcohol, ethyl cellosolve, butyl cellosolve, butyl carbitol, propylene glycol monobutyl ether, propylene glycol monomethyl ether, dipropylene glycol monomethyl ether, propylene glycol mono-propyl ether and acetone.

As examples of the precursor of the first compound mentioned above, the followings may be given: salts such as aluminum nitrate, cerium nitrate, cerium acetate, titanyl sulfate and ammonium molybdate, methyl triethoxysilane, methyl trimethoxysilane, tetraethoxysilane, tetramethoxysilane, tetraisopropoxysilane, tetraisopropoxytitanium, tetrabutoxytitanium, tetrabutoxyzirconium, triisopropoxyaluminum and the like or a condensate thereof.

As examples of the neutralizing agent and the hydrolysis catalyst mentioned above, the followings may be given:
the neutralizing agent: ammonia, sodium hydroxide, potassium hydroxide and the like; basic hydrolysis catalysts: monoethanolamine, diethanolamine, triethanolamine, ammonia, ethylenediamine, t-butylamine, γ-aminopropyltriethoxysilane, N-2-aminoethyl-3-aminopropyltriethoxysilane, N-2-aminoethyl-3-aminopropyl methyl dimethoxy silane, urea, sodium silicate, sodium hydroxide and the like; and acidic hydrolysis catalysts: oxalic acid, acetic acid, nitric acid, sulfuric acid, phosphoric acid, phosphonic acid and the like.

As mentioned above, as the first compound, particularly silicon oxide and/or polysiloxane condensate is preferred. As a method of forming the first coating layer therefrom, in the case of silicon oxide, for example, any method capable of stirring or kneading the metallic pigment and a solution containing a silicon compound in a slurry or paste state with the mixture being kept at basic or acidic condition may be adopted, and thereby the first coating layer composed of silicon oxide can be formed on the surface of the metallic pigment; in the case of polysiloxane condensate, for example, the metallic pigment and alkoxysilane are put together, and alkoxysilane is hydrolyzed and condensated to form the first coating layer composed of polysiloxane condensate on the surface of the metallic pigment. It should be noted that the present invention is not limited to the mentioned methods.

<Coloring Pigment>

Although the coloring pigment of the present invention is adhered to the surface of the first coating layer, as to be described hereinafter, in the case where a layer of an organic compound having a phosphate group or a carboxyl group is formed on the first coating layer, the coloring pigment may be adhered to the surface of the layer of the organic compound. Therefore, unless otherwise specified, the expression of "coloring pigment adhered to the surface of the first coating layer" in the present invention not only means that the coloring pigment is adhered directly to the surface of the first coating layer but also means that the coloring pigment is adhered to the surface of the layer of the organic compound.

In the present invention, the metallic pigment mentioned above is configured to have a main effect of imparting a metallic luster and thus it is generally achromatic, and the coloring pigment is configured to have a main effect of imparting a chromatic color but it is not limited thereto, for example, the coloring pigment may function to impart an achromatic color such as white or black.

Any publicly known pigment may be used as the coloring pigment mentioned above without any particular limitation. For example, the followings may be given as examples.

In other words, organic pigments such as a diketopyrrolopyrrole-based pigment, a quinacridone-based pigment, a dioxazine-based pigment, an isoindolinone-based pigment, a condensed azo-based pigment, a threne-based pigment, a perynone-based pigment, a perylene-based pigment, a quinophthalone-based pigment or a phthalocyanine-based pigment, and an inorganic pigment such as iron oxide or carbon black may be used.

Specifically, phthalocyanine, halogenated phthalocyanine, quinacridone, diketopyrrolopyrrole, isoindolinone, azomethine metal complex, indanthrone, perylene, perinone, anthraquinone, dioxazine, benzoimidazolone, condensed azo, triphenylmethane, quinophthalone, anthrapyrimidine, iron oxide, ultramarine blue, iron blue, cobalt blue, chrome green, bismuth vanadate, fired composite oxide pigment, carbon black, titanium black, titanium dioxide, ultrafine titanium dioxide, zinc oxide, chromium oxide, zirconium oxide, iron oxide red, iron oxide black, iron oxide yellow, chromium hydroxide, cobalt aluminum oxide, cobalt titanate, aluminum hydroxide, barium sulfate, talc, kaolin, mica, bentonite, magnesium silicate, aluminum silicate, anhydrous silicic acid, hydrous silicic acid, manganese violet, aluminum, gold, titanium mica, bismuth oxychloride and the like may be given as examples.

From the consideration of adhesive property, weather resistance and coloring power to the metallic pigment, the followings are particularly preferred as examples of the coloring pigment: phthalocyanine blue, phthalocyanine green, quinacridone red, quinacridone maroon, quinacridone gold, diketopyrrolopyrrole, isoindolinone yellow, isoindolinone orange, anthrapyrimidine yellow, dioxazine violet, perylene maroon, azomethine copper complex, transparent iron oxide, carbon black, ultrafine titanium oxide and the like.

Besides the pigments exemplified above, it is possible to use various tar dyes permitted to be used as cosmetic preparations and pharmaceutical preparations in Japan or abroad, inorganic pigments or the like satisfying Japanese Standards of Cosmetic Ingredients.

For example, the followings defined by the Pharmaceutical Affairs Law of Japan (names in brackets are defined by the United States Food and Drug Administration) may be given as examples of the coloring pigment of the present invention: Red No. 2 (FD&C Red No. 2), Red No. 3 (FD&C Red No. 3), Red No. 102, Red No. 104(1) (D&C Red No. 28), Red No. 105(1), Red No. 106, Yellow No. 4 (FD&C Yellow No. 5), Yellow No. 5 (FD&C Yellow No. 6), Green No. 3 (FD&C Green No. 3), Blue No. 1 (FD&C Blue No. 1), Blue No. 2 (FD&C Blue No. 2), Red No. 201 (D&C Red No. 6), Red No. 202 (D&C Red No. 7), Red No. 203 (D&C Red No. 8), Red No. 204 (D&C Red No. 9), Red No. 205 (D&C Red No. 10), Red No. 206 (D&C Red No. 11), Red No. 207 (D&C Red No. 12), Red No. 208 (D&C Red No. 13), Red No. 213 (D&C Red No. 19), Red No. 214, Red No. 215 (D&C Red No. 37), Red No. 218 (D&C Red No. 27), Red No. 219, Red No. 220 (D&C Red No. 34), Red No. 221 (D&C Red No. 35), Red No. 223 (D&C Red No. 21), Red No. 225 (D&C Red No. 17), Red No. 226 (D&C Red No. 30), Red No. 227 (D&C Red No. 33), Red No. 228, Red No. 230(1) (D&C Red No. 22), Red No. 230(2), Red No. 231, Red No. 232, Orange No. 201 (D&C Orange No. 5), Orange No. 203 (D&C Orange No. 17), Orange No. 204, Orange No. 205 (D&C Orange No. 4), Orange No. 206, Orange No. 207, Yellow No. 201 (D&C Yellow No. 7), Yellow No. 202(1) (D&C Yellow No. 8), Yellow No. 202(2), Yellow No. 203 (D&C Yellow No. 10), Yellow No. 204 (D&C Yellow No. 11), Yellow No. 205, Green No. 201 (D&C Green No. 5), Green No. 202 (D&C Green No. 6), Green No. 204 (D&C Green No. 8), Green No. 205, Blue No. 201 (D&C Blue No. 6), Blue No. 202, Blue No. 203, Blue No. 204 (D&C Blue No. 9), Blue No. 205 (D&C Blue No. 4), Brown No. 201 (D&C Brown No. 1), Violet No. 201 (D&C Violet No. 2), Red No. 401 (EXT. D&C Red No. 3), Red No. 404, Red No. 405, Red No. 501, Red No. 502, Red No. 503, Red No. 504 (FD&C Red No. 4), Red No. 505, Red No. 506, Orange No. 401, Orange No. 402 (EXT. D&C Orange No. 3), Orange No. 403 (EXT. D&C Orange No. 4), Yellow No. 401 (EXT. D&C Yellow No. 7), Yellow No. 402, Yellow No. 403 (EXT. D&C Yellow No. 7), Yellow No. 404, Yellow No. 405, Yellow No. 406 (EXT. D&C Yellow No. 1), Yellow No. 407 (EXT. D&C Yellow No. 3), Green No. 401 (EXT. D&C Green No. 1), Green No. 402, Blue 403, Blue No. 404, Violet No. 401 (EXT. D&C Violet No. 2), Black No. 401 (D&C Black No. 1), aluminum lake, barium lake, zirconium lake and the like of each of the abovementioned dyes defined in the Pharmaceutical Affairs Law.

Among the above examples, from the consideration of formulation to cosmetics, adhesive property and coloring power to the metallic pigment, the followings are particularly preferred as examples of the coloring pigment: Red No. 202, Red No. 203, Red No. 204, Red No. 205, Red No. 206, Red No. 207, Red No. 208, Red No. 219, Red No. 220, Red No. 221, Red No. 228, Orange No. 203, Orange No. 204, Blue No. 205, Red No. 404, Red No. 405, Orange No. 401, Yellow No. 401, Blue No. 404, Red No. 2 aluminum lake, Red No. 3 aluminum lake, Red No. 102 aluminum lake, Red No. 104(1) aluminum lake, Red No. 105(1) aluminum lake, Red No. 106 aluminum lake, Red No. 230(1) aluminum lake, Yellow No. 4 aluminum lake, Yellow No. 5 aluminum lake, Yellow No. 203 aluminum lake, Blue No. 1 aluminum lake, Blue No. 2 aluminum lake, iron blue, ultramarine blue, titanium oxide, zinc oxide, chromium oxide, zirconium oxide, iron oxide red, iron oxide black, iron oxide yellow, chromium hydroxide, cobalt aluminum oxide, cobalt titanate, aluminum hydroxide, barium sulfate, talc, kaolin, mica, bentonite, magnesium silicate, manganese violet, carbon black, bismuth oxychloride and the like.

The primary particle size of the coloring pigment is not particularly limited, and thus, the coloring pigment having a primary particle size preferably in the range of 0.01 µm to 1 µm and more preferably in the range of 0.02 µm to 0.1 µm can be used. When the primary particle size is 0.01 µm or more, it is easy to disperse the coloring pigment; and when the primary particle size is 1.0 µm or less, it is easy to uniformly adhere the coloring pigment to the surface of the metallic pigment.

The adhering amount of the coloring pigment is preferably 1 part or more by mass to 200 parts or less by mass, and more preferably 5 parts or more by mass to 100 parts or less by mass with respect to 100 parts by mass of the metallic pigment. The adhering amount may be adjusted appropriately according to the specific surface area of the metallic pigment. If the adhering amount is less than 1 part by mass, sufficient color saturation may not be obtained for the final colored metallic pigment; on the other hand, if the adhering amount is more than 200 parts by mass, the brightness of the final colored metallic pigment may be weakened.

In order to improve the adhesive property of the coloring pigment, it is more preferable that the surface of the metallic pigment is treated with a compound such as any of the following compounds.

Specifically, the compounds may include but not be limited thereto, for example, ethylene diamine, trimethylene diamine, tetramethylene diamine, pentamethylene diamine, hexamethylene diamine, 1,7-diaminoheptane, 1,8-diaminooctane, 1,10-diaminodecane, 1,12-diaminododecane, o-phenylenediamine, m-phenylenediamine, p-phenylenediamine, 1,8-diaminonaphthalene, 1,2-diaminocyclohexane, stearyl propylene diamine, N-β-(aminoethyl)-γ-aminopropyltrimethoxysilane, N-β-(aminoethyl)-γ-aminopropyl methyl dimethoxy silane, N-2-aminoethyl-3-aminopropyl-methyldimethoxysilane, benzoic acid, vinyl benzoate, salicylic acid, anthranilic acid, m-aminobenzoic acid, o-aminobenzoic acid, p-aminobenzoic acid, 3-amino-4-methyl benzoic acid, p-amino salicylic acid, 1-naphthoic acid, 2-naphthoic acid, naphthenic acid, 3-amino-2-naphthoic acid, cinnamic acid, aminocinnamic acid and the like.

<Layer of Organic Compound Having Phosphate Group or Carboxyl Group>

The colored metallic pigment of the present invention can have a layer of an organic compound having a phosphate group or an organic compound having a carboxyl group, and the layer of the organic compound is formed on the first coating layer. In this case, the coloring pigment is adhered to the surface of the layer of the organic compound, constituting a preferred embodiment of the present invention. In other words, the layer of the organic compound having a phosphate group or a carboxyl group functions to improve the adhesive property of the coloring pigment.

It is inferred that the layer of the organic compound having a phosphate group or a carboxyl group is formed through chemical or physical adsorption of the organic compound having a phosphate group or a carboxyl group on the surface of the first coating layer. Further, the layer of the organic compound may be formed on the surface of the first coating layer as a layer or may be formed spotting on the surface without forming a layer. In other words, the layer of the organic compound having a phosphate group or a carboxyl group in the present invention includes not only a case where the organic compound is present on the first coating layer in a form of a continuous layer but also a case where the organic compound is present on the first coating layer in a form of being spotted without forming a layer. Essentially, the layer of the organic compound having a phosphate group or a carboxyl group in the present invention is not limited in forms as long as it exists at an amount corresponding to the adhering amount of the coloring pigment to be adhered later.

Forming on the surface of the first coating layer a layer of the organic compound having a phosphate group or a carboxyl group improves the adhesive property of the coloring pigment to be adhered later, and provides the colored metallic pigment with a high color saturation. Further, it is possible to inhibit the detachment of the coloring pigment in the case where the colored metallic pigment is dispersed in a solvent or a paint.

Here, the organic compound having a phosphate group refers to a compound having a structure in which a part of OH groups of phosphoric acid is substituted by an organic substituent group, and is also called an organic phosphate compound. The organic compound having a carboxyl group refers to the so-called carboxylic acid.

In the present invention, it is preferable that the organic compound having a carboxyl group is a carboxylic acid having at least one double bond and two or more carboxyl groups or a polymer of the carboxylic acid. As the polymer, a thermally polymerized carboxylic acid is particularly preferred. The thermally polymerized carboxylic acid refers to a carboxylic acid having one double bond or more and two carboxyl groups or more, which is obtained by thermally polymerizing at least one type of carboxylic acid having a double bond.

As a starting raw material for the thermally polymerized carboxylic acid, for example, 3-octenoic acid, 10-undecenoic acid, oleic acid, linoleic acid, elaidic acid, acrylic acid and linolenic acid each having a double bond and a carboxyl group (i.e., a carboxylic acid having a double bond), and industrially available fatty acid mixture such as tall oil fatty acid, palm oil fatty acid, rice bran oil fatty acid, linseed oil fatty acid and soybean oil fatty acid may be given as examples, and they may be used independently or in a combination of at least two types. More specifically, for example, a product prepared from the thermal polymerization of linseed oil fatty acid, soybean oil fatty acid or acrylic acid may be used as the raw material.

Further, as examples of the thermally polymerized carboxylic acid, commercially available products such as HARIDIMER 200, HARIDIMER 300 and DIACID 1550 (trademark, manufactured by Harima Chemicals Group, Inc.), Pripol 1017 (trademark, manufactured by Uniqema), Empol 1008 (trademark, manufactured by Cognis), Yunidaimu 27 (trademark, manufactured by Arizona Chemical Co.) and Basadaimu 216 (trademark, manufactured by Henkel Japan Ltd.) may be given.

The use of such thermally polymerized carboxylic acid mentioned above allows the coloring pigment to be adsorbed uniformly and stably onto the surface of the first coating layer, enabling the colored metallic pigment with a dark color. Thus, the coloring pigment is difficult to liberate, and stable even when being formulated into cosmetic preparations, making it possible to obtain a colored metallic pigment superior in safety.

As mentioned above, the organic compound having a phosphate group refers to a compound (organic phosphate compound) having a structure in which a part of OH groups of phosphoric acid is substituted by an organic substituent group. Such organic phosphate compound is not particularly limited, and may be an organic phosphate ester. As examples of organic phosphate ester, such as stearyl acid phosphate, myristyl acid phosphate, palmityl acid phosphate, lauryl acid phosphate, polyoxyethylene alkylphenyl ether acid phosphate, n-decyl acid phosphate, 2-ethylhexyl acid phosphate, oleyl acid phosphate, hexyl acid phosphate, butyl acid phosphate and ethylene glycol acid phosphate may be given.

It is preferable that the organic compound having a phosphate group is an organic phosphate compound having at least one polymerizable double bond (that is, a compound structured to have at least one polymerizable double bond and have a part of OH groups of phosphoric acid substituted by an organic substituent group). As an example of such compound, for example, an organic phosphoric acid ester having at least one polymerizable double bond may be given. As example of the organic phosphoric acid ester having at least one polymerizable double bond, for example, organic phosphate compounds having one polymerizable double bond such as oleyl acid phosphate, mono(2-acryloyloxyethyl) acid phosphate, mono(2-methacryloyloxyethyl) acid phosphate, 2-acryloyloxyethyl acid phosphate, 2-methacryloyloxyethyl acid phosphate, (2-hydroxyethyl) methacrylate acid phosphate, 2-methacryloyloxyethyl acid phosphate, 2-acryloyloxyethyl acid phosphate, diphenyl-2-methacryloyloxy ethyl acid phosphate, diphenyl-2-acryloyloxyethyl acid phosphate, dibutyl-2-methacryloyloxyethyl acid phosphate, dibutyl-2-acryloyloxyethyl acid phosphate, dioctyl-2-methacryloyloxyethyl acid phosphate, dioctyl-2-acryloyloxyethyl acid phosphate and 2-methacryloyloxy propyl acid phosphate, and organic phosphate compounds having two or more polymerizable double bonds such as bis(2-chloroethyl) vinyl phosphonate, di-2-methacryloyloxyethyl acid phosphate, tri-2-methacryloyloxyethyl acid phosphate, di-2-acryloyloxyethyl acid phosphate, tri-2-acryloyloxyethyl acid phosphate and diallyl dibutyl phosphono succinate may be given.

The organic compound having a phosphate group used to form the layer of the organic compound having a phosphate group is preferably a compound having at least one polymerizable double bond, and more preferably a compound having two or more polymerizable double bonds, for the purpose of improving the adhesive property of the coloring pigment even better.

The presence of the organic compound having a phosphate group can be identified according to the detection and quantitative determination of P (phosphorus) by ICP (Inductively Coupled Plasma) analysis or the like.

The amount of the organic compound having a phosphate group or a carboxyl group is not particularly limited, and may be 0.1 parts or more by mass to 10 parts or less by mass, and more preferably 0.5 parts or more by mass to 5 parts or less by mass with respect to 100 parts by mass of the metallic pigment with the first coating layer formed thereon. If the amount is 0.1 parts or more by mass, it is advantageous in terms of the adhesive property of the coloring pigment, and if the amount is 10 parts or less by mass, it is advantageous in terms of film performances of the coating film or the like using the colored metallic pigment (if the amount is excessively great, the adhesive property and the weather resistance will degrade) and in terms of safety when the colored metallic pigment is used as a cosmetic preparation.

<Second Coating Layer>

In the colored metallic pigment according to the present invention, it is preferable that a second coating layer is further formed on the coloring pigment adhered to the surface of the first coating layer. The formation of the second coating layer makes the adhesion of the coloring pigment stronger and the water resistance better.

The composition of the second covering layer is not particularly limited, and may be composed of a radical-polymerizable resin or the first compound, similar to the first coating layer. Thereby, the second coating layer is a layer which is dense and excellent in solvent resistance and water resistance, making the liberation and quality degradation of the coloring pigment less likely to occur.

Further, the method for forming the second coating layer is not particularly limited, and the same method for forming the first coating layer may be employed. The thickness of the second coating layer is not particularly limited, and may be 5 nm or more to 200 nm or less in terms of the water resistance and pigment liberation of the colored metallic pigment (which will be insufficient if the thickness is less 5 nm) and in terms of the outer appearance of the coating composition such as the coating film or the outer appearance of the cosmetic product (which will be deteriorated if the thickness is greater than 200 nm). The thickness may be determined according to a measuring method through observing sections of the colored metallic pigment by using a scanning electron microscope or the like.

<Method for Producing Colored Metallic Pigment>

The method to be conducted for producing the colored metallic pigment of the present invention includes a first step of preparing a coated metallic pigment having the first coating layer formed on the surface of the metallic pigment, and a second step of adhering the coloring pigment to the surface of the first coating layer of the coated metallic pigment.

As mentioned above, the first coating layer is formed from the radical-polymerizable resin or the first compound which have been described in the above. Each step will be described in more detail hereinafter.

<First Step>

The first step of the present invention is a step of preparing the coated metallic pigment having the first coating layer formed on the surface of the metallic pigment. The preparation of the coated metallic pigment having the first coating layer formed on the surface of the metallic pigment may be done by purchasing a commercially available coated metallic pigment having the mentioned configuration, or may be done by preparing the metallic pigment without the first coating layer and thereafter forming the first coating layer on the surface of the metallic pigment according to the method described above in relation to the first coating layer.

<Second Step>

The second step of the present invention is a step of adhering the coloring pigment to the surface of the first coating layer of the coated metallic pigment. The method for adhering the coloring pigment to the surface of the first coating layer of the coated metallic pigment is not particularly limited, and may be any method listed in the following, for example.

Specifically, firstly in a first stage, the coloring pigment is dispersed in a solvent, and preferably in a non-polar solvent to produce a dispersion (slurry) of the coloring pigment. As mentioned above, for the purpose of surface-treating the coloring pigment with a specific compound such as ethylene diamine so as to improve the adhesive property of the coloring pigment, it is acceptable to add the specific compound to the dispersion. It is also acceptable to add a surfactant or a dispersant such as a chelate compound to the dispersion if necessary.

Aliphatic hydrocarbons or aromatic hydrocarbons having a boiling point in the range of about 100° C. to 250° C., or a mixture thereof may be preferably used as the nonpolar solvent. Specifically, normal paraffin, isoparaffin, toluene, xylene, solvent naphtha, kerosene, mineral spirit, petroleum benzine and the like may be given as examples but the nonpolar solvent is not limited thereto. If necessary, a small amount of alcohol or ester-based solvent may be added as an adjuvant for dispersing the coloring pigment.

The method of dispersing the coloring pigment is not particularly limited, for example, a dispersion method using a grinding medium such as a ball mill, a bead mill or a sand mill may be used. The dispersion time is not particularly limited, and is preferably in the range of 30 minutes to 30 hours in consideration of the design effect of the colored metallic pigment (the design effect will decrease if the dispersion time is less than 30 minutes) and the productivity thereof (the productivity will become worse if the dispersion time is longer than 30 hours). The dispersion temperature is not particularly limited, and may be in the range of 0° C. to 100° C.

Next, in a second stage, the metallic pigment having the first coating layer formed thereon (i.e., the coated metallic pigment) is added to the above-prepared dispersion of the coloring pigment and is further dispersed to adhere the coloring pigment to the surface of the first coating layer. As the dispersion method in this case, in addition to the dispersion method mentioned above, stirring by using a stirrer or a disperser is also suitable.

The dispersion time in the second stage is not particularly limited, and is preferably in the range of 30 minutes to 30 hours in consideration of the degree of dispersion of the coloring pigment (the pigment may not be dispersed well if the dispersion time is less than 30 minutes) and the productivity thereof (the productivity will decrease if the dispersion time is longer than 30 hours). The dispersion temperature is not particularly limited, and may be in the range of 0° C. to 100° C.

Through the second step as mentioned above, it is possible to obtain the colored metallic pigment of the present invention having the coloring pigment adhered to the surface of the first coating layer of the coated metallic pigment. As can be apparently seen from the above description, the adhesion of the coloring pigment to the surface of the first coating layer is considered to be chemical adsorption or physical adsorption.

It should be noted that in the above description the first stage and the second stage are conducted separately, but it is not necessary that they have to be conducted in this order, a method in which the order of the first and second stages is reversed or a method in which all the components used in the first and second stages are added and dispersed at one time may be employed as long as it will not affect the effects of the present invention.

<Additional Step>

The method for producing the colored metallic pigment of the present invention may include an additional step of forming a layer of an organic compound having a phosphate group or a carboxyl group by adsorbing the organic compound to the surface of the first coating layer of the coated metallic pigment after the first step, and in this case, the abovementioned second step becomes a step of adhering the coloring pigment onto the layer of the organic compound formed in the additional step. The additional step improves the adhesive property of the coloring pigment which will be adhered in the second step.

The method for adsorbing the organic compound having a phosphate group or a carboxyl group to the surface of the first coating layer of the coated metallic pigment is not particularly limited, and may be performed according to the following method, for example.

Specifically, the coated metallic pigment may be put into contact with a solution prepared by dissolving the organic compound having a phosphate group or a carboxyl group in a solvent as listed below, and dispersed at a predetermined temperature for a predetermined time to adsorb the organic compound to the surface of the first coating layer of the coated metallic pigment.

As examples of the abovementioned solvent, the followings may be given: methanol, ethanol, 1-propanol, isopropyl alcohol, n-butanol, s-butanol, t-butanol, glycerin, allyl alcohol, ethylene glycol, ethylene glycol monoethyl ether, ethylene glycol monomethyl ether, ethylene glycol monomethoxy methyl ether, diethylene glycol, propylene glycol monobutyl ether, acetone, acetyl acetone, methylethyl ketone, diethyl ketone, cyclohexanone, diacetone alcohol, methyl isobutyl ketone, methyl-n-butyl ketone, methyl-n-propyl ketone, dimethyl sulfoxide and the like.

Any method for processing the organic compound and the coated metallic pigment in a slurry state or any method for mixing them in a paste state may be employed but not limited thereto as the method of putting the coated metallic pigment into contact with the organic compound. The processing temperature is not limited as well, and may be 5° C. or more to 100° C. or less and preferably 30° C. or more to 70° C. or less. The processing time is not particularly limited as well, and may be 1 minute or more to 180 minutes or less and preferably 10 minutes or more to 60 minutes or less.

It should be noted that in the case where the additional step is conducted, the second step may be conducted in a manner similar to that mentioned in the above. In other words, it is possible to employ a method, for example, to add the coated metallic pigment with a layer of the organic compound having a phosphate group or a carboxyl group formed on the surface thereof to the dispersion of the coloring pigment and disperse it therein.

<Third Step>

The method for producing the colored metallic pigment of the present invention may include a third step of forming a second coating layer on the coloring pigment after the second step. Accordingly, the adhesion of the coloring pigment is made stronger and the water resistance thereof is further improved.

The third step is not particularly limited, and thus, the second coating layer may be formed by a similar method to the method for forming the first coating layer.

<Paint Composition>

The present invention also relates to a paint composition formulated with the colored metallic pigment mentioned above, and the paint composition of the present invention includes an ink composition. Generally, the composition includes the colored metallic pigment, a resin component and a solvent. Particularly, a water-based paint composition using a hydrophilic solvent as the solvent is superior in water resistance, stable and excellent in color development.

The content of the colored metallic pigment formulated in the paint composition of the present invention is preferably 0.1 parts or more by mass to 50 parts or less by mass, and more preferably 1 part or more by mass to 30 parts or less by mass with respect to 100 parts by mass of the resin component. If the colored metallic pigment is less than 0.1 part by mass, the design effect cannot be obtained as desired, and if the colored metallic pigment is more than 50 parts by mass, the image clarity of the coating film will be degraded.

The content of the solvent formulated in the paint composition of the present invention is preferably 1 part or more by mass to 100 parts or less by mass, and more preferably 5 parts or more by mass to 50 parts or less by mass with respect to 100 parts by mass of the resin component. If the solvent is less than 1 part by mass, the dispersion of the colored metallic pigment in the paint composition is insufficient, and if the solvent is more than 100 parts by mass, the solvent evaporated upon drying and curing the paint will be an issue of environmental pollution.

The resin component to be formulated in the paint composition of the present invention is not particularly limited, and the followings may be given as examples: thermosetting acrylic resin/melamine resin, thermosetting acrylic resin/CAB (cellulose acetate butyrate)/melamine resin, thermosetting polyester (alkyd) resin/melamine resin, thermosetting polyester (alkyd)/CAB/melamine resin, isocyanate-curable urethane resin/cold setting acrylic resin, and water-dilutable acrylic emulsion/melamine resin.

The solvent to be formulated in the paint composition of the present invention is not particularly limited, and may be water, an alcohol-based or glycol-based or ketone-based or ester-based hydrophilic solvent (such as methyl alcohol, ethyl alcohol, isopropyl alcohol, n-propyl alcohol, t-butyl alcohol, n-butyl alcohol, isobutyl alcohol, ethyl cellosolve, butyl cellosolve, butyl carbitol, propylene glycol monobutyl ether, propylene glycol monomethyl ether, dipropylene glycol monomethyl ether, propylene glycol mono-propyl ether, acetone, ethyl acetate or propyl acetate), or an oil-based solvent such as aromatic solvent or alicyclic solvent or hydrocarbon-based solvent (such as benzene, toluene, xylene, hexane, heptane, cyclohexane, octane or mineral spirit).

In addition, an additive such as a pigment dispersing agent, an antifoaming agent, an anti-settling agent or a curing catalyst and other coloring pigments may be formulated in the paint composition if necessary.

<Plastic Material>

The present invention also relates to a plastic material formulated with the colored metallic pigment mentioned above. The plastic material includes not only a resin molded body blended and kneaded with the colored metallic pigment (final molded article) but also a work-in-process intermediate object before the final molding such as a synthetic resin coloring master batch which contains the colored metallic pigment to be formulated into matrix resin for the purpose of coloring the matrix resin or colored pellets which are obtained by kneading the synthetic resin coloring master batch and the matrix resin to be colored into pellet shape.

The resin constituting the plastic material is not particularly limited, and specifically, polyethylene, polypropylene, chlorinated polyethylene, ethylene-vinyl acetate copolymer, polyvinyl chloride, polystyrene, acrylic resin, polycarbonate, polyamide, polyimide, ABS resin, AS resin or the like may be used alone or in a combination of two types or more.

Generally, the content of the colored metallic pigment may be in the range of about 0.005 to 500 parts by mass and preferably in the range of about 0.005 to 2 parts by mass with respect to 100 parts by mass of the resin. However, the content may be beyond the abovementioned range, depending on the properties of the colored metallic pigment to be used, the types of the resin, and the usage of the final product.

<Cosmetic Preparation>

The present invention also relates to a cosmetic preparation formulated with the colored metallic pigment mentioned above. The colored metallic pigment of the present invention has a hiding power superior to pearl pigments in particular, and thereby can provide a bright hue for cosmetic preparations containing water.

The type of the cosmetic preparation formulated with the colored metallic pigment of the present invention is not particularly limited, and makeup cosmetic preparations such as lipstick, foundation, blusher, eyeshadow, nail enamel and mascara, hair cosmetic preparations such as hair gel, hair wax, hair treatment, shampoo and hair manicure, and basic cosmetic preparations such as lotion, foundation cream and sun block may be given as specific examples.

Besides the colored metallic pigment of the present invention, the other components constituting the cosmetic preparations may include, for example, oils and fats (olive oil, castor oil etc.), waxes (beeswax, carnauba wax, lanolin etc.), hydrocarbon oils (liquid paraffin, squalane, polybutene etc.), fatty esters (isopropyl myristate, cetyl 2-ethylhexanate, diisopropyl adipate, glyceryl trimyristate etc.), higher fatty acids (oleic acid, isostearic acid etc.), higher alcohols (isostearyl alcohol, oleyl alcohol etc.), silicone oils (dimethyl polysiloxane, methylphenyl polysiloxane etc.) and fluorine compounds (perfluoropolyether etc.).

If necessary, surfactant, humectant, polyvalent alcohol, water-soluble polymer, film former, water-insoluble polymer, polymer emulsion, powder, pigment, dyestuff, lake, lower alcohol, ultraviolet absorber, vitamins, antioxidant, anti-fungus agent, perfume and the like may be formulated into the cosmetic preparation.

The content of the colored metallic pigment in the cosmetic preparation, for example, may be preferably in the range of 0.1 to 99% by mass, and more preferably in the range of 1 to 80% by mass.

Formulation method of the colored metallic pigment is not particularly limited, and thereby, any common method for producing cosmetic preparations can be used. As the dispersion method, a disperser, a roll mill or the like is suitable.

EXAMPLES

Hereinafter, the present invention will be described in more detail by way of Examples, but the present invention is not limited thereto.

Example 1

First Step

First, aluminum pigment was used as the metallic pigment. The aluminum pigment was processed into a paste form by washing a paste containing the aluminum pigment (trademark: "5620NS" manufactured by Toyo Aluminum K. K., average particle size: 18 μm) with mineral spirit and filtering the same thereafter. The non-volatile component (aluminum pigment) in the paste after filtration was 70% by mass (the remainder was mineral spirit).

214 g of the paste (150 g in terms of solid content) and 2000 g of mineral spirit were added to a 3 L separable flask and stirred into a slurry. Under continuous stirring, nitrogen gas was introduced to turn the system into nitrogen atmosphere. After that, the temperature was raised to 80° C.

Then, 0.75 g of acrylic acid serving as a monomer constituting the first coating layer, 6.75 g of trimethylol propane trimethacrylate, 7.50 g of epoxidized polybutadiene (which was diluted to 50% by mass by using mineral spirit), 3.75 g of styrene, and 0.75 g of azobis isobutyronitrile (AIBN) serving as a polymerization initiator were added to the slurry, and the monomers were subjected to radical polymerization to form on the surface of the aluminum pigment the first coating layer composed of radical-polymerizable resin.

After 8 hours from the addition of AIBN, the system was cooled to terminate reaction. Subsequently, the slurry was filtered and washed with mineral spirit in small amount, and thereby the coated metallic pigment was prepared, with the first coating layer composed of the radical-polymerizable resin formed on the surface of the metallic pigment.

<Additional Step>

The coated metallic pigment prepared in the first step was washed with propylene glycol monomethyl ether. Then, 150 g (in terms of solid content) of the coated metallic pigment after being washed was introduced to a solution obtained by dissolving 1.5 g (1% by mass with respect to the coated metallic pigment) of di-2-methacryloyloxyethyl acid phosphate serving as the organic compound having a phosphate group (hereinafter, referred to as "organic phosphate compound" as well) in 400 g of propylene glycol monobutyl ether, and stirred at 75° C. for 1 hour to offer a slurry. The obtained slurry was subjected to solid-liquid separation to offer a paste (solid content at 70% by mass) of a precursor of the colored metallic pigment formed with a layer of the organic compound having a phosphate group (hereinafter, referred to as "organic phosphate compound layer" as well) through adsorption of the organic phosphate compound to the surface of the first coating layer.

Second Step 20 g of commercially available phthalocyanine blue pigment (trademark: "LIONOL BLUE 7185-PM" (average primary particle size of 0.02 μm) manufactured by Toyo Ink Co. Ltd) serving as the coloring pigment, 0.5 g of N-2-aminoethyl-3-aminopropyl methyl dimethoxy silane (2.5% by mass with respect to the coloring pigment), and 30 g of mineral spirit were added into a pot mill having a diameter of 5 cm and an internal volume of 500 cc and loaded with 500 g of glass beads having a diameter of 1 mm, and the coloring pigment was subjected to ball milling dispersion for 24 hours.

Thereafter, 42.9 g (30 g in terms of solid content) of the paste of the precursor of the colored metallic pigment obtained after the additional step and 30 g of mineral spirit were added into the pot mill mentioned above to undergo ball milling dispersion for another 1 hour. Through this step, the coloring pigment was adhered to the surface of the organic phosphate compound layer in the precursor of the colored metallic pigment.

The obtained slurry was washed with 500 g of mineral spirit to separate the desired product from glass beads, and after filtration, the colored metallic pigment (colored aluminum pigment) of the present invention having the coloring pigment adhered to the surface of the organic phosphate compound layer which was formed on the first coating layer was obtained.

Third Step

To a slurry obtained by dispersing 20 g of the colored metallic pigment (in terms of solid content) obtained in the above in 200 g of mineral spirit, 0.3 g of acrylic acid, 0.3 g of trimethylolpropane triacrylate, 0.3 g of styrene, and 0.3 g of epoxidized polybutadiene were added, and thereafter, while the mixture was being heated and stirred at 80° C. under nitrogen atmosphere, 0.05 g of azobis isobutyronitrile was added as a polymerization initiator to make the monomers undergo radical polymerization, and thereby, the second coating layer composed of radical-polymerizable resin was formed on the coloring pigment of the colored metallic pigment obtained in the above second step.

After this treatment, the slurry was subjected to solid-liquid separation to provide the colored metallic pigment of the present invention having the second coating layer formed on the coloring pigment in a paste form (solid content at 60% by mass).

Example 2

First Step

In a similar manner to Example 1, 200 g (in terms of solid content) of the coated metallic pigment was prepared.

Additional Step

The coated metallic pigment prepared in the first step was washed with propyleneglycol monomethyl ether. Then, 150 g (in terms of solid content) of the coated metallic pigment after being washed was introduced to a solution obtained by dissolving 1.5 g (1% by mass with respect to the coated metallic pigment) of mono(2-methacryloyloxyethyl) acid phosphate serving as the organic phosphate compound in 400 g of propylene glycol monobutyl ether, and stirred at 75° C. for 1 hour to offer a slurry. The obtained slurry was subjected to solid-liquid separation to offer a paste (solid content at 70% by mass) of a precursor of the colored metallic pigment formed with the organic phosphate compound layer through adsorption of the organic phosphate compound to the surface of the first coating layer.

Second Step 20 g of commercially available diketopyrrolopyrrole pigment (trademark: "IRGAZIN DPP Rubine TR" (average particle size of 0.02 μm) manufactured by BASF) serving as the coloring pigment, 0.5 g of o-amino benzoic acid (2.5% by mass with respect to the coloring pigment), and 30 g of mineral spirit were added into a pot mill having a diameter of 5 cm and an internal volume of 500 cc and loaded with 500 g of glass beads having a diameter of 1 mm, and the coloring pigment was subjected to ball milling dispersion for 24 hours.

Thereafter, 42.9 g (30 g in terms of solid content) of the paste of the precursor of the colored metallic pigment obtained after the additional step mentioned above and 30 g of mineral spirit were added into the pot mill mentioned above to undergo ball milling dispersion for another 1 hour. Through this step, the coloring pigment was adhered to the surface of the organic phosphate compound layer in the precursor of the colored metallic pigment.

The obtained slurry was washed with 500 g of mineral spirit to separate the desired product from glass beads, and after filtration, the colored metallic pigment (colored aluminum pigment) of the present invention having the coloring pigment adhered to the surface of the organic phosphate compound layer formed on the first coating layer was obtained.

Example 3

The colored metallic pigment (in the state of a paste containing solid content at 60% by mass) of the present invention was prepared in the same manner as in Example 1 except that the coated metallic pigment prepared in the following manner was used to replace the coated metallic pigment prepared in the first step in Example 1.

Specifically, 0.5 g of metallic molybdenum powder was added gradually to 10 g of hydrogen peroxide solution containing hydrogen peroxide at 30% by mass, and the solution obtained after reaction was dissolved in 600 g of isopropyl alcohol (hereinafter referred to as "IPA").

Next, 143 g (100 g in terms of solid content) of aluminum pigment (trademark: "5620NS" manufactured by Toyo Aluminum K. K., average particle size: 18 μm) was added as the metallic pigment to the IPA solution obtained above, and mixed through stirring at 50° C. for 1 hour to offer a slurry. Thereby, the first coating layer was formed from molybdenum oxide on the surface of the aluminum pigment serving as the metallic pigment.

Subsequently, ammonia water and 20 g of water were added to the slurry to adjust pH value of the slurry to 8.5. Then, 40 g of tetraethoxy silane dissolved in 100 g of IPA was slowly dropped into the slurry after pH adjustment, and mixed through stirring at 75° C. for another 2 hours. After that, the slurry was subjected to solid-liquid separation by using a filter to offer the coated metallic pigment formed with another first coating layer from polysiloxane condensate (first compound) on the first coating layer mentioned above. Thus, the coated metallic pigment is formed with the first coating layers in a double-layer structure.

Example 4

The colored metallic pigment (in the state of a paste containing solid content at 60% by mass) of the present invention was prepared in the same manner as in Example 1 except that the additional step was not conducted in contrast to Example 1. In other words, the colored metallic pigment in the present example has such a structure that the coloring pigment is adhered to the surface of the first coating layer which is formed on the surface of the metallic pigment and a second coating layer is formed on the coloring pigment.

Example 5

The colored metallic pigment (in the state of a paste containing solid content at 60% by mass) of the present invention was prepared in the same manner as in Example 3 except that the additional step was not conducted in contrast to Example 3. In other words, the colored metallic pigment in the present example has such a structure that the coloring pigment is adhered to the surface of the first coating layer which is formed on the surface of the metallic pigment and a second coating layer is formed on the coloring pigment.

Example 6

The colored metallic pigment (in the state of a paste containing solid content at 60% by mass) of the present invention was prepared in the same manner as in Example 1 except that oleyl acid phosphate was used to replace di-2-methacryloyloxyethyl acid phosphate used in the additional step in Example 1.

Example 7

The colored metallic pigment (in the state of a paste containing solid content at 60% by mass) of the present invention was prepared in the same manner as in Example 2 except that the coated metallic pigment prepared in the following manner was used to replace the coated metallic pigment prepared in the first step in Example 2.

Specifically, 143 g (100 g in terms of solid content) of aluminum pigment (trademark: "5620NS" manufactured by Toyo Aluminum K. K., average particle size: 18 μm) was added as the metallic pigment to 500 g of propyleneglycol monomethyl ether, and dispersed with the liquid temperature kept at 18° C. Then, a solution prepared by dissolving 5 g of ammonium paramolybdate $((NH_4)_6Mo_7O_{24}.4H_2O)$ in 100 g of deionized water was added slowly to the dispersion solution, and stirred for 1 hour with the temperature of the solution kept at 15 to 20° C. After that, the slurry was subjected to solid-liquid separation by using a filter to offer the coated metallic pigment having the first coating layer formed from molybdenum oxide on the surface of the metallic pigment.

Example 8

The colored metallic pigment (colored aluminum pigment) of the present invention having the coloring pigment adhered to the first coating layer was prepared through the same steps as in Example 2 except that the additional step was not conducted in contrast to Example 2.

Example 9

First Step 200 g (in terms of solid content) of the coated metallic pigment was prepared in a similar manner to the first step of Example 1.

Additional Step 143 g of the coated metallic pigment prepared in the first step mentioned above was dispersed in 500 g of mineral spirit, and 3.6 g of a thermopolymerized carboxylic acid (trademark: "DIACID 1550" manufactured by Harima Chemicals Group, Inc.) having a double bond and thermally polymerized from acrylic acid and soybean oil fatty acid was added as the organic compound having a carboxyl group into the dispersion solution, and the mixture was stirred vigorously at 90° C. for 1 hour under nitrogen gas atmosphere.

Then, the dispersion solution obtained in the above manner was cooled to room temperature, and subjected to solid-liquid separation to provide the aluminum pigment treated with the thermopolymerized carboxylic acid (the coated metallic pigment formed with the layer of the organic compound having a carboxyl group) in which the non-volatile component was 60% by mass.

Second Step

The colored metallic pigment of the present invention was obtained by conducting the second step of Example 1 on the aluminum pigment treated with the thermopolymerized carboxylic acid obtained in the above. The colored metallic pigment has a structure in which the coloring pigment is adhered to the surface of the layer of the organic compound (thermopolymerized carboxylic acid) which has a carboxyl group and is formed on the first coating layer.

Example 10

First Step 10 g of hydrogen peroxide solution containing 30% by mass of hydrogen peroxide was dissolved in 500 g of IPA, and 40 g of aluminum pigment (trademark: "5422NS" manufactured by Toyo Aluminum K. K.) was further added as the metallic pigment, and mixed through stirring at 75° C. for 1 hour to provide a slurry. Thereafter, ammonia water and 80 g of water were added to the slurry to adjust the pH value of the slurry to 10.0. Then, 40 g of tetraethoxy silane dissolved in 40 g of IPA was slowly dropped into the slurry, and mixed through stirring at 75° C. for another 2 hours. After that, the slurry was subjected to solid-liquid separation by using a filter to form an amorphous silicon oxide film (the first coating layer composed of the first compound) on the surface of the metallic pigment.

Additional Step and Second Step 200 g (in terms of solid content) of the coated metallic pigment prepared as mentioned in the above was subjected to the additional step and the second step in a similar manner to Example 9 to provide the colored metallic pigment of the present invention. Namely the colored metallic pigment has a structure in which the coloring pigment is adhered to the surface of the layer of the organic compound (the layer of the thermopolymerized carboxylic acid) which has a carboxyl group and is formed on the first coating layer which is an amorphous silicon oxide film.

Example 11

First Step, Additional Step and Second Step

The colored metallic pigment was prepared in the same manner as in Example 10 except that commercially available Red No. 202 (manufactured by Kishi Kasei) was used to replace the phthalocyanine blue pigment which was used as the coloring pigment in the second step of Example 10.

Third Step 30 g of the colored metallic pigment obtained as mentioned above was dispersed in 200 g of IPA to provide a slurry, and 5 g of tetraethoxysilane and 15 g of urea aqueous solution at 10% by mass were added to the slurry and mixed through stirring at 75° C. for 5 hours to form on the coloring pigment of the colored metallic pigment an amorphous silicon oxide film which was the second coating layer composed of the first compound. Thereby, the colored metallic pigment of the present invention was prepared. Namely, the colored metallic pigment has such a structure that the coloring pigment is adhered to the surface of the layer of the organic compound having a carboxyl group, the layer of the organic compound is formed on the first coating layer, and the second coating layer is formed on the coloring pigment.

Comparative Example 1

The colored metallic pigment (in the state of a paste containing solid content at 60% by mass) was prepared in the same manner as in Example 1 except that a metallic pigment without the first coating layer (in other words, aluminum pigment (trademark: "5620NS" manufactured by Toyo Aluminum K. K., average particle size: 18 μm) serving as the metallic pigment) was prepared to replace the coated metallic pigment prepared in the first step of Example 1 and the additional step was not conducted as well.

Comparative Example 2

The colored metallic pigment (in the state of a paste containing solid content at 60% by mass) was prepared in the same manner as in Example 2 except that aluminum pigment with an iron oxide layer coating the surface thereof (trademark "Paliocrom Gold L2020" (particle size 20 μm) manufactured by BASF) was prepared to replace the coated metallic pigment prepared in the first step of Example 2 and the additional step was not conducted as well.

Comparative Example 3

The colored metallic pigment (in the state of a paste containing solid content at 60% by mass) was prepared in the same manner as in Example 2 except that aluminum pigment, the surface of which was treated with inorganic phosphoric acid, was prepared in the following manner to replace the coated metallic pigment prepared in the first step of Example 2 and the additional step was not conducted as well.

Specifically, 20 g of isopropyl alcohol solution containing 1.0 g of phosphoric acid was added to 143 g (100 g in terms of solid content) of commercially available aluminum pigment (trademark: "5620NS" manufactured by Toyo Aluminum K. K., average particle size: 18 μm) and kneaded for 5 minutes, and thereby, the aluminum pigment having phosphate groups adsorbed to the surface thereof was prepared and used.

Comparative Example 4

143 g of commercially available aluminum pigment (trademark: "5620NS" manufactured by Toyo Aluminum K. K., average particle size: 18 μm) and 3.6 g of a thermopolymerized carboxylic acid (trademark: "DIACID 1550" manufactured by Harima Chemicals Group, Inc.) having a double bond and thermally polymerized from acrylic acid and soybean oil fatty acid were added to 500 g of mineral spirit, and stirred vigorously at 90° C. for 1 hour under nitrogen gas atmosphere.

Then, the dispersion liquid obtained in the above manner was cooled to room temperature, and thereafter subjected to solid-liquid separation to provide the aluminum pigment treated with the thermopolymerized carboxylic acid in which the non-volatile component was 60% by mass.

Thereafter, as in Example 1, the aluminum pigment treated with the thermopolymerized carboxylic acid was subjected to the second step and the subsequent steps of Example 1 to provide the colored metallic pigment. The colored metallic pigment has a structure in which a coating layer is formed from thermopolymerizable resin instead of the first coating layer of the present invention.

The following tests were conducted by using the colored metallic pigments obtained as mentioned above from Examples 1 to 11 and Comparative Examples 1 to 4.

<Test 1>

2.5 g of each of the colored metallic pigments obtained from Examples 1 to 11 and Comparative Examples 1 to 4 was dispersed in 50 g of commercially available acrylic lacquer (trademark: "Auto Clear" manufactured by Nippon Paint Co., Ltd.) to prepare a paint, and the paint was applied to a piece of double-sided art paper by using a 250 μm doctor blade to prepare a coated plate.

The color saturation value of each coated plate prepared in the above manner was measured by using a multi-angle spectrophotometer (trademark: "X-Rite MA-68II" manufactured by X-Rite Inc.). The color saturation value ($C^*$) was calculated according to the following expression, using values $a^*$ and $b^*$ measured at an incident angle of 45° and an offset angle of 15°, respectively. The greater the color saturation value (C*) is, the higher the color saturation will be. The results are shown in Table 1.

Color saturation value $(C^*)=(a^{*2}+b^{*2})^{1/2}$

<Test 2>

After 0.2 g of the solid content of each of the colored metallic pigments obtained from Examples 1 to 11 and Comparative Examples 1 to 4 and 20 g of ethyl acetate were added to a 20-ml test tube and dispersed with thoroughly shaking, the mixture was stood still for 3 hours, and the elution pattern of the coloring pigment was observed. In this test, in the case where the adhering force of the coloring pigment is insufficient, the supernatant fluid will be colored by the eluted coloring pigment, while in the case where the adhering force is sufficient, the supernatant fluid will be transparent. The degree of transparency of the supernatant fluid was evaluated through visual observation and listed in the following by four levels. The closer the supernatant fluid becomes colorless and transparent, it denotes that the color development will be more stable (i.e., the adhesive property of the coloring pigment is higher). The results are shown in Table 1.

A: colorless and transparent
B: transparent but slightly colored
C: transparent but colored
D: opaque and colored <Test 3>

Water-based paint compositions were prepared in the following manner by using the colored metallic pigments obtained from Examples 1 to 11 and Comparative Examples 1 to 4.

<Preparation of Rheology-Controlling Agent>

19.5 parts by mass of a polyamide-based rheology-controlling agent (trademark: "Disparlon AQ600" manufactured by Kusumoto Chemicals, Ltd.), 6 parts by mass of butyl cellosolve and 106.5 parts by mass of ion-exchanged water were mixed through stirring for 1 hour to prepare a rheology-controlling agent (composition 1).

<Preparation of Resin Solution>

27.9 parts by mass of an acryl copolymer (trademark: "Setaqua 6802" manufactured by Neuplex), 16.8 parts by mass of polyurethane dispersion A (trademark: "Bayhydrol XP 2621" manufactured by Bayer Material Science), 4.1 parts by mass of polyurethane dispersion B (trademark: "Bayhydrol PT241" manufactured by Bayer Material Science), 1.9 parts by mass of a melamine resin solution (trademark: "Cymel327" manufactured by Mitsui Cytec Ltd.), 5.3 parts by mass of butyl cellosolve, 0.3 parts by mass of an anti-foaming/leveling agent (trademark: "AQ7120" manufactured by Kusumoto Chemicals, Ltd.), and 12.4 parts by mass of ion-exchanged water were mixed, and stirred for 30 minutes or longer to prepare a resin solution (composition 2).

<Preparation of Metallic Base>

0.4 parts by mass of a dispersant (trademark: "AQ320" manufactured by Kusumoto Chemicals, Ltd.) and butyl cellosolve were added to each (4.4 parts by mass in terms of solid content) of the color metallic pigments obtained from Examples 1 to 11 and Comparative Examples 1 to 4 to make the total amount equal to 15.00 parts by mass, and the resultant was mixed through stirring for 10 minutes to prepare the metallic base (composition 3).

<Preparation of Water-Based Paint Composition>

10.5 parts by mass of the metallic base (composition 3) was added to 96.2 parts by mass of the resin solution (composition 2), and mixed through stirring for 10 minutes or longer. Next, 12.3 parts by mass of the rheology-controlling agent (composition 1) was added gradually to the mixture, and mixed through stirring for another 10 minutes. Then, 10% dimethylethanolamine aqueous solution was added to make the pH value of the mixture equal to 8.3±0.1, and mixed through stirring for another 10 minutes or longer. Finally, a proper amount of ion-exchanged water was added to make the viscosity equal to a reference value (25 seconds as measured with Ford cup No. 4), and mixed through stirring for 10 minutes or longer. The product thus prepared was used as the water-based paint composition.

Each water-based paint composition prepared in the above manner was sampled at 80 g, stored for 7 days in a water bath vessel with the temperature thereof adjusted to 50° C., and the accumulated amount of hydrogen gas generated thereby was measured by using a measuring cylinder according to water substitution method. The less the gas generation amount is, the better the water resistance will be. The results are shown in Table 1.

TABLE 1

|  | Test 1 | Test 2 | Test 3 (Unit: ml) |
|---|---|---|---|
| Example 1 | 75.8 | A | 0.1 |
| Example 2 | 82.5 | A | 0.2 |
| Example 3 | 76.7 | A | 0.3 |
| Example 4 | 59.3 | B | 0.0 |
| Example 5 | 55.8 | B | 0.5 |
| Example 6 | 69.5 | A | 0.0 |
| Example 7 | 70.6 | A | 0.5 |
| Example 8 | 67.2 | B | 0.3 |
| Example 9 | 73.9 | B | 0.3 |
| Example 10 | 83.1 | A | 0.0 |
| Example 11 | 78.2 | A | 0.0 |
| Comparative Example 1 | 52.3 | C | 6.8 |
| Comparative Example 2 | 64.1 | C | 3.5 |
| Comparative Example 3 | 51.5 | C | 7.9 |
| Comparative Example 4 | 68.5 | B | 5.3 |

As seen apparently from Table 1, it is obvious that the colored metallic pigment according to each of the Examples is superior in water resistance, stable in color development and high in color saturation in comparison to the colored metallic pigment of each of the Comparative Examples.

Example 12

A nail enamel was prepared as a cosmetic preparation according to the following formulation by using the colored metallic pigment of Example 11, and compared with a commercially available conventional cosmetic preparation.

(1) nitrocellulose (viscosity: ½ sec): 6.5 parts by mass
(2) nitrocellulose (viscosity: ⅛ sec): 11.0 parts by mass
(3) toluene sulfonamide resin: 12.5 parts by mass
(4) acetotributyl citrate: 5.3 parts by mass
(5) camphor: 1.0 part by mass
(6) n-butyl alcohol: 0.5 parts by mass
(7) ethyl alcohol: 4.5 parts by mass
(8) ethyl acetate: 15.0 parts by mass
(9) butyl acetate: 30.0 parts by mass
(10) colored metallic pigment: 13.7 parts by mass In comparison to the commercially available conventional nail enamel (obtained by replacing the colored metallic pigment in the above formulation with the pearl pigment and Red No. 202), the nail enamel obtained according to the present example is superior in hiding power and gloss, and brilliant in color.

Embodiments and specific examples of the present invention are described above. However, proper combinations of the constitutions of the respective embodiments and the respective specific examples are also originally intended.

It should be understood that the embodiments and the examples disclosed herein have been presented for the purpose of illustration and description but not limited in all aspects. It is intended that the scope of the present invention is not limited to the description above but defined by the scope of the claims and encompasses all modifications equivalent in meaning and scope to the claims.

The invention claimed is:

1. A colored metallic pigment comprising
a metallic pigment, a first coating layer formed on the surface of said metallic pigment, and a coloring pigment, wherein,
said first coating layer is a radical-polymerizable resin or a first compound,
said first compound is an oxide or a hydroxide of at least one element selected from the group consisting of Al, Si, Ti, Cr, Zr, Mo and Ce, and
said coloring pigment is adhered to the surface of a layer of an organic compound having a phosphate group or a carboxyl group, said layer of the organic compound being disposed on said first coating layer.

2. The colored metallic pigment according to claim 1, wherein said organic compound having a carboxyl group is a carboxylic acid having at least one double bond and two or more carboxyl groups, or a polymer of the carboxylic acid.

3. The colored metallic pigment according to claim 1, wherein said organic compound having a phosphate group is an organic phosphate compound having at least one polymerizable double bond.

4. The colored metallic pigment according to claim 1, wherein a second coating layer is disposed on said coloring pigment.

5. The colored metallic pigment according to claim 4, wherein said second coating layer is a radical-polymerizable resin or a first compound.

6. The colored metallic pigment according to claim 1, wherein said metallic pigment is an aluminum pigment.

7. The colored metallic pigment according to claim 1, wherein said radical-polymerizable resin is the radical polymerization product of a monomer and/or an oligomer having at least one polymerizable double bond.

8. The colored metallic pigment according to claim 1, wherein said first compound is silicon oxide and/or polysiloxane condensate.

9. A paint composition comprising the colored metallic pigment of claim 1.

10. A plastic material comprising the colored metallic pigment of claim 1.

11. A cosmetic preparation comprising the colored metallic pigment of claim 1.

12. A method for producing a colored metallic pigment, comprising:
a first step of preparing a coated metallic pigment having a first coating layer formed on the surface of a metallic pigment;
a second step of adhering a coloring pigment to the surface of said first coating layer of said coated metallic pigment,
said first coating layer being formed from a radical-polymerizable resin or a first compound,
said first compound being an oxide or a hydroxide of at least one element selected from the group consisting of Al, Si, Ti, Cr, Zr, Mo and Ce; and
after said first step, an additional step of forming, on the surface of said first coating layer of said coated metallic pigment, a layer of an organic compound having a phosphate group or a carboxyl group,
said coloring pigment, in said second step, being adhered onto the layer of said organic compound formed in said additional step.

* * * * *